United States Patent [19]

Sangekar et al.

[11] 3,957,662
[45] May 18, 1976

[54] PHARMACEUTICAL LUBRICANTS

[75] Inventors: Surendra Anandrao Sangekar, Elizabeth, N.J.; Prabhakar Ranchhordas Sheth, Nanuet, N.Y.

[73] Assignee: Hoffmann-La Roche Inc., Nutley, N.J.

[22] Filed: Aug. 8, 1972

[21] Appl. No.: 279,133

[52] U.S. Cl................................. 252/11; 252/33.2; 252/33.6; 252/39; 252/40.5
[51] Int. Cl.² ................... C10M 1/40; C10M 1/54; C10M 1/24; C10M 3/18
[58] Field of Search................... 252/11, 33.2, 33.6, 252/40.5, 39

[56] References Cited
UNITED STATES PATENTS

| | | | |
|---|---|---|---|
| 3,408,297 | 10/1968 | Sheldahl | 252/33.2 |
| 3,518,345 | 6/1970 | Dines et al. | 252/11 |
| 3,719,599 | 3/1973 | Crivellaro et al. | 252/11 |

*Primary Examiner*—Delbert E. Gantz
*Assistant Examiner*—I. Vaughn
*Attorney, Agent, or Firm*—Samuel L. Welt; Bernard S. Leon; R. Hain Swope

[57] ABSTRACT

Improved pharmaceutical lubricants comprising finely divided magnesium or calcium stearate coated with a surfactant are disclosed. The improved lubricants greatly enhance disintegration and dissolution time of tablets and capsules prepared therefrom without loss in essential pharmaceutical lubricant properties.

2 Claims, No Drawings

PHARMACEUTICAL LUBRICANTS

BACKGROUND OF THE INVENTION

Magnesium and calcium stearates have long been recognized in the art of pharmaceutical compounding as lubricants and are probably the most common pharmaceutical lubricants in use at the present time. These substances, however, in spite of their wide acceptance in the pharmaceutical arts as lubricants have certain disadvantages.

The primary disadvantage to the use of magnesium and calcium stearate as pharmaceutical lubricants lies in the fact that they are extremely hydrophobic. This hydrophobicity hinders dissolution and disintegration time of solid dosage forms containing magnesium and calcium stearates. Another factor which acts to hinder dissolution and disintegration time of solid dosage forms containing magnesium or calcium stearate is their electrostatic attraction with therapeutically active substances and other excipients. This electrostatic attraction is particularly pronounced when calcium and magnesium stearate are utilized in finely divided particulate form, i.e., an average particle size in the range of from 1 to 15 microns. This disadvantage of magnesium and calcium stearates is not uncommon, however, as there are in the literature numerous reports of other common pharmaceutical excipients inhibiting the dispersion of particles of active drug in the gastric media as a result of hydrophobicity. Other commonly utilized pharmaceutical compounding excipients act to impede dissolution in various ways in addition to being hydrophobic such as, for example, by forming an insoluble film around the active drug particle or by chemically complexing the active drug particles.

One attempt which has been made to remedy the problems caused by the hydrophobicity of many pharmaceutical compounding excipients is the inclusion of surfactants into solid dosage forms containing them to improve dispersibility. Where surfactants are utilized, however, they are, for the most part, utilized in such minute quantities that homogeneous distribution throughout the dosage form is virtually impossible.

It has been suggested to form an itimate mixture of surfactants with certain acidic substances for incorporation into effervescent tablets. U.S. Pat. No. 3,151,986 discloses such mixtures wherein fumaric and adipic acid are "coated" with a surfactant prior to incorporation into effervescent tablets. It is stated therein that the "coated" particles of acid are more free-flowing during preparation of the tablets and are more soluble in water than uncoated particles. The "coating" of such particles, however, protects them until such time as they enter into the required acid-base reaction in the presence of water. In effervescent tablets, acid particles must in fact usually be protected within the tablet to prevent premature reaction with the base. It is therefore clear that such "coated" particle substrates have no positive function either of the preparation of the tablet or in the tablet itself and the substrates do not function until the "coating" is removed.

In view of the foregoing, it is considered unexpected that coating particles of magnesium or calcium stearate with a surfactant in accordance with the invention produces particles free of the disadvantageous hydrophobicity characteristic of these pharmaceutical lubricants in conventional uncoated form yet umimpeded in lubricant efficaciousness. The fact that magnesium or calcium stearate particles coated with a surfactant in accordance of the invention are equal to uncoated particles as pharmaceutical lubricants is particularly surprising when it is considered that the surfactants which are utilized to coat them exert a negative effect on lubricity when present in uncombined form.

BRIEF DESCRIPTION OF THE INVENTION

The present invention is directed to improved pharmaceutical lubricants comprising finely particulate magnesium or calcium stearate coated with from about 1% to about 5% preferably from about 2% to about 3% by weight, of a surfactant based on the weight of said magnesium or calcium stearate.

DETAILED DESCRIPTION OF THE INVENTION

In accordance with the present invention, improved pharmaceutical lubricants are prepared by coating magnesium or calcium stearate with from about 1% to about 5%, preferably from about 2% to bout 3% by weight of a surfactant based on the weight of said magnesium or calcium stearate. The resultant improved lubricants are dispersible in cold water and are unexpectedly vastly superior in disintegration and dissolution time to similar tablets prepared with conventional uncoated magnesium or calcium stearate. Additionally, a distinct improvement in tablet hardness and friability is realized utilizing the coated lubricants of the invention when compared to tablets prepared with uncoated magnesium or calcium stearate. These advantages are obtained without loss of the essential lubricant properties of magnesium or calcium stearate as would be expected by coating them with a substance which, by itself, has negative lubricity.

The surfactant utilized to coat magnesium and calcium stearates in accordance with the present invention can be selected from the many commercially available surfactants of the anionic or non-ionic types. In practicing the invention, however, it is preferred to utilize non-ionic surfactants such as, for example, the dialkyl esters of sodium sulfosuccinate containing between 7 and 11 carbon atoms in each of their alkyl chains and anionic surfactants such as, for example, ethylene oxide ethers of partial esters of sorbitol anhydrides and sodium lauryl sulfate containing from 10 to 30 ethylene oxide units. Especially preferred in the practice of the invention, in addition to sodium lauryl sulfate, are dioctyl sodium sulfosuccinate and polyoxyethylene (20) sorbitan monooleate. These three surfactants are commercially available as Duponol C manufactured by E. I. DuPont de Nemours and Co., Wilmington, Del., Aerosol OT manufactured by American Cyanamide Co., New York, New York, and Tween 80 manufactured by Atlas Powder Co., Wilmington, Del., respectively.

It is contemplated that the amount of surfactant utilized in the preparation of the improved pharmaceutical lubricants of the invention will comprise from about 1% by weight to about 5% by weight, preferably from about 2% to about 3% by weight of the magnesium or calcium stearate. It is further contemplated that the magnesium or calcium stearate as utilized herein will be of a finely divided, particulate character. Generally, it is preferred that the magnesium and calcium stearate to be coated in accordance with the invention will have an average particle size between about 5 and 10 microns and substantially all of the particles thereof will be between 1 and 25 microns.

The improved pharmaceutical lubricants of the invention are prepared by spray drying a solution of the surfactant in a suitable solvent in which has been suspended finely divided, particulate magnesium or calcium stearate. Suitable solvents include, for example, ethanol, isopropanol, water and the like, with water being preferred. The equipment utilized in performing this spray drying operation is not critical to the invention and may be selected from any commercial equipment recognized in the art as being capable of performing spray drying operations. By spray drying a suspension of finely divided, particulate magnesium or calcium stearate in a surfactant-containing solution, dry, free-flowing lubricant powders are obtained wherein each particle of magnesium or calcium stearate is substantially uniformly coated with an ultrafine layer of surfactant.

The improved pharmaceutical lubricants prepared in accordance with the invention may be utilized in all pharmaceutical operations wherein the use of magnesium or calcium stearate is considered to be conventional. A particular area of applicability lies in the production of tablets from any therapeutically active substance available in a dry form. Such therapeutically active substances include compounds from all recognized classifications of pharmaceutical and therapeutic activity. The only limitations on the choice of a therapeutically active substance which can be formulated into tablets and capsules with the improved lubricant of the invention are those substances which are recognized as not being amenable to the production of such dosage forms. The amount of the improved lubricants of the invention which is to be utilized in the preparation of such tablets and capsules is not critical as such amounts correspond to the amount of prior art uncoated magnesium and calcium stearate utilized in such preparations. The method of forming tablets from formulations containing the improved lubricants of the invention may be any method commonly recognized in the art. It is to be noted that the improved lubricants of the invention are especially useful in the preparation of tablets by the direct compression of a dry blend of tablet ingredients.

It is also within the scope of the invention to utilize the coated magnesium and calcium stearates of the invention as pharmaceutical lubricants in any proportions with each other as well as individually. Such combinations are completely within the discretion of one skilled in the art of pharmaceutical compounding. The quantities of such combinations to be utilized in any given instance are analogous to amounts of uncoated magnesium and calcium stearate utilized in combination in the prior art.

The improved pharmaceutical lubricants of the invention are also useful in the preparation of dry compositions which are to be filled into capsules. In this respect, good lubricity is critical to the unimpeded flow of such a dry formulation through automatic capsule filling equipment. The improved lubricants of the present invention possess the same efficaciousness as uncoated magnesium and calcium stearate in capsule filling on automatic equipment and additionally have been found to materially increase the dissolution of the capsule and contents after ingestion.

The improved disintegration and dissolution times of solid dosage forms, e.g. tablets, capsules and the like prepared from the improved lubricants of the present invention are of importance in all areas of therapeutics. This is so as it is important to have as much of a therapeutic dosage regimen available in the body as possible in the shortest possible time for rapid onset of therapeutic activity. Rapid onset of therapeutic activity is especially critical in certain therapeutic situations. One such situation concerns the therapeutic treatment of Parkinsonism with L-dopa. The effectiveness of L-dopa in this instance is known to be based on the amount of drug which can pass the blood-brain barrier intact. It is therefore apparent that a dosage form which would release more active drug in a shorter time period such as is afforded by the present invention would be a valuable adjunct to L-dopa therapy as the use of such a dosage form would allow for a maximum amount of active drug to be available for absorption within a given time period. In addition to L-dopa therapy, dosage forms having improved disintegration and dissolution rates such as are afforded by the present invention are also especially useful in treating insomnia with a therapeutic compound such as, for example, flurazepam hydrochloride. In this instance, the rapid availability of a therapeutic dosage is important to allow the patient to fall asleep in the shortest possible period of time.

In addition to the therapeutic active ingredients, tablets and capsules prepared utilizing the improved pharmaceutical lubricants of the invention may contain any other therapeutically adjunct materials recognized in the art of pharmaceutical compounding. Such adjuncts include, for example, binders, disintegrants, excipients, sweeteners, preservatives, flavoring agents, buffers and the like.

The following examples further illustrate the invention.

EXAMPLE 1

To illustrate the superior dissolution of compositions containing the improved coated magnesium stearate lubricant of the present invention when compared to conventional uncoated magnesium stearate, capsules were filled with the following formulations containing flurazepam hydrochloride as the active ingredient

| Ingredient | mg/Capsule | |
|---|---|---|
| | Coated | Control |
| Flurazepam Hydrochloride | 15.3 | 15.3 |
| Lactose anhydrous | 269.5 | 269.7 |
| Corn starch dry | 30.0 | 30.0 |
| Talc USP | 10.0 | 10.0 |
| Magnesium stearate | — | 10.0 |
| Magnesium stearate coated with 2% by weight dioctyl sulfosuccinate | 10.2 | — |
| Total per Capsule | 335 | 335 |

The dissolution of these capsules was determined in artificial gastric juice according to the procedure set forth in the USP XVII. The results are reported in the following table:

TABLE

| Time in Minutes | % Dissolved | |
|---|---|---|
| | Coated | Control |
| 10 | 77 | 13 |
| 20 | 96 | 39 |
| 30 | 100 | 65 |

The results in the Table clearly indicate that the capsule containing magnesium stearate coated with a surfactant in accordance with the present invention is superior to an identical capsule prepared with conventional uncoated magnesium stearate.

EXAMPLE 2

To determine the effect, if any, coating magnesium stearate with a surfactant in accordance with the invention has on the lubricity thereof, placebo tablets were prepared as follows.

| Ingredient | mg/Tablet | |
|---|---|---|
|  | Coated | Control |
| Lactose, anhydrous | 173.73 | 173.75 |
| STA-Rx 1500* | 25.00 | 25.00 |
| Magnesium stearate | — | 1.25 |
| Magnesium stearate coated with 2% dioctyl sodium sulfosuccinate | 1.27 | — |
| Total Tablet | 200 | 200 |

*Direct compression grade starch manufactured by A.E. Staley Co. Decatur, Ill.

The tablets were formed at 2,000 psi on a Carver press, punch size 8/32 inch s.c., scored, and the ejection pressure was noted. As the ejection pressure for each formula was 20–40 lbs. it can be concluded that there is no significant difference in the lubricity of the two formulae.

EXAMPLE 3

Placebo tablets were prepared containing about 5% conventional magnesium stearate and magnesium stearate coated in accordance with the invention, respectively. These tablets were tested on a Strong-Cobb Hardness Tester in the tablet containing the magnesium stearate coated in accordance with the invention was found to be slightly harder.

| Ingredients | mg/Tablet | |
|---|---|---|
|  | Coated | Control |
| Lactose, anhydrous | 221.25 | 221.75 |
| STA-Rx 1500 | 25.00 | 25.00 |
| Magnesium stearate | — | 12.25 |
| Magnesium stearate coated with 2% dioctyl sodium sulfosuccinate | 12.75 | — |
| Total Weight | 250 | 250 |
| Average hardness, Strong-Cobb Units | 8 | 6 |
| Punch Size 11/32" S.C. scored | | |

EXAMPLE 4

Ascorbic acid tablets were prepared according to the following formulation and were tested for disintegration, friability and hardness.

| Ingredient | mg/Tablet | | | |
|---|---|---|---|---|
| Ascorbic acid as a 90% granulation | 585 | 585 | 585 | 585 |
| Microcrystalline cellulose | 24 | 24 | 24 | 24 |
| Magnesium stearate | 3 | — | — | — |
| Magnesium stearate coated with 2% dioctyl sodium sulfosuccinate | — | 3 | — | — |
| Calcium stearate | — | — | 3 | — |
| Calcium stearate coated with 2% dioctyl sodium stearate | — | — | — | 3 |
| Total Tablet Weight | 612 | 612 | 612 | 612 |
| Hardness S.C.U. | 10 | 20 | 10 | 13 |
| Friability | 2 of 20 capped | 0.23% | 4 of 20 capped | 0.27% |
| Disintegration Minutes | 15 | 10 | 14 | 14 |

In this particular experiment, calcium stearate coated in accordance with the invention was not observed to improve disintegration time. However, the tablets containing coated calcium stearate show a substantial improvement in hardness and an exceptional improvement in friability. The friability tests were carried out in a Roche Friabilitor wherein weighed tablets are subjected to repeated droppings from about 12 inches in a plastic drum. After about 100 such droppings the tablets are removed and weighed. The percent figures given above where no capping occurred represent the weight lost by the tablets over their original weight. From the foregoing data it can be seen that the tablets containing the coated lubricants of the invention are clearly an improvement over tablets containing uncoated lubricants. This improvement is especially apparent with calcium stearate as 4 of 20 tablets prepared with the uncoated lubricant capped (pieces of the convex surface of the tablet split off) whereas only 0.27% weight loss was experienced with tablets containing coated calcium stearate.

EXAMPLE 5

Capsules were filled with the following formulations containing a water-soluble therapeutically active compound, i.e. flurazepam hydrochloride and the dissolution thereof after 10 minutes in artificial gastric juice was determined as in Example 1.

| Ingredient | mg/Capsule | | | |
|---|---|---|---|---|
|  | Control | Coated A | Coated B | Coated C |
| Flurazepam HCl | 30.6 | 30.6 | 30.6 | 30.6 |
| Lactose anhydrous | 256.4 | 256.2 | 256.2 | 256.08 |
| Corn starch, dry NCS | 33.0 | 33.0 | 33.0 | 33.0 |
| Magnesium stearate | 10.0 | — | — | — |
| Magnesium stearate coated | | | | |

-continued

| Ingredient | mg/Capsule | | | |
|---|---|---|---|---|
| | Control | Coated A | Coated B | Coated C |
| with 2% by weight polyoxyethylene (20) sorbitan mono-oleate | — | 10.2 | — | — |
| Magnesium stearate coated with 2% by weight sodium lauryl sulfate | — | — | 10.2 | — |
| Magnesium stearate coated with 3% by weight dioctyl sodium sulfosuccinate | — | — | — | 10.32 |
| Total Capsule | 330 mg | 330 mg | 330 mg | 330 mg |
| Dissolution after 10 minutes | 41% | 69% | 100% | 100% |

EXAMPLE 6

Tablets were prepared in a Carver Press at 3000 lb pressure from the following formulations utilizing as the active ingredient a combination of sulfamethoxazole and trimethoprim and the disintegration time noted as in Example 4

| Ingredient | mg/Tablet | | | |
|---|---|---|---|---|
| | Control | Coated A | Coated B | Coated C |
| Sulfamethoxazole | 400.00 | 400.00 | 400.00 | 400.00 |
| Trimethoprim | 80.00 | 80.00 | 80.00 | 80.00 |
| Microcrystalline cellulose | 150.00 | 150.00 | 150.00 | 150.00 |
| Corn starch, USP | 10.00 | 10.00 | 10.00 | 10.00 |
| Starch for paste | 40.00 | 40.00 | 40.00 | 40.00 |
| Methylcellulose 400 cps | 9.00 | 9.00 | 9.00 | 9.00 |
| Certified colors | 6.50 | 6.50 | 6.50 | 6.50 |
| Magnesium stearate | 2.00 | — | — | — |
| Magnesium stearate coated with 2% by weight sodium lauryl sulfate | — | 2.04 | — | — |
| Magnesium stearate coated with 3% by weight dioctyl sodium sulfosuccinate | — | — | 2.06 | — |
| Magnesium stearate coated with 2% by weight ethylene oxide (20) adduct of sorbitan mono-oleate | — | — | — | 2.04 |
| Total Tablet Weight | 697.5 mg | 697.54 mg | 697.56 mg | 697.54 mg |
| Disintegration time in seconds | 195 | 125 | 150 | 145 |

EXAMPLE 7

Tablets were prepared containing as the active ingredient L-Dopa with conventional calcium stearate and calcium stearate coated in accordance with the invention as follows:

| Ingredient | mg/Tablet | |
|---|---|---|
| | Coated | Control |
| L-Dopa | 505.0 | 505.0 |
| Amylopectin | 5.0 | 5.0 |
| Polyvinylpyrrolidone | 5.0 | 5.0 |
| Microcrystalline cellulose | 169.5 | 169.5 |
| Calcium stearate | — | 5.0 |
| Calcium stearate coated with 2% by weight dioctyl sodium sulfosuccinate | 5.0 | — |
| Certified color | 0.5 | 0.5 |
| | 690.0 | 690.0 |

The dissolution rate of these tablets was determined in accordance with the procedure of the USP XVII. The results are reported in the following table utilizing six tablets per test.

TABLE

| Time in Minutes | % Dissolved | | | |
|---|---|---|---|---|
| | Coated | | Control | |
| | Average | Range | Average | Range |
| 2.5 | 64 | 55–73 | 48 | 29–61 |
| 5 | 93 | 90–95 | 89 | 84–93 |
| 10 | 98 | 95–100 | 96 | 93–99 |
| 15 | 98 | 96–101 | 97 | 95–100 |
| 20 | 99 | 96–101 | 98 | 96–100 |

The results set forth in the above table clearly demonstrate the superiority of calcium stearate coated in accordance with the invention over conventional uncoated calcium stearate.

We claim

1. An improved pharmaceutical lubricant composition consisting essentially of finely divided magnesium stearate, calcium stearate or mixtures thereof substantially uniformly coated with from about 1% by weight to about 5% by weight based on the weight of said magnesium or calcium stearate of surfactant selected from the group consisting of sodium lauryl sulfate, polyoxyethylene (20) sorbitan mono-oleate and dioctyl sodium sulfosuccinate.

2. The improved lubricant composition of claim 1 wherein said coating comprises from about 2% to about 3% by weight based on the weight of said magnesium or calcium stearate.

* * * * *